(12) United States Patent
Challa et al.

(10) Patent No.: US 10,357,345 B2
(45) Date of Patent: Jul. 23, 2019

(54) AUTOMATIC FILLING MECHANISM AND METHOD FOR A HAND-HELD ORAL CLEANING DEVICE

(71) Applicant: KONINKLIJKE PHILIPS N.V., Eindhoven (NL)

(72) Inventors: Vinod Challa, Bothell, WA (US); Brian Johanski, Snohomish, WA (US); Lewis McFadyen, Hong Kong (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 179 days.

(21) Appl. No.: 15/540,104

(22) PCT Filed: Dec. 18, 2015

(86) PCT No.: PCT/IB2015/059756
§ 371 (c)(1),
(2) Date: Jun. 27, 2017

(87) PCT Pub. No.: WO2016/108131
PCT Pub. Date: Jul. 7, 2016

(65) Prior Publication Data
US 2017/0367800 A1    Dec. 28, 2017

Related U.S. Application Data

(60) Provisional application No. 62/097,261, filed on Dec. 29, 2014.

(51) Int. Cl.
*A61C 17/02* (2006.01)
*B67D 7/02* (2010.01)

(52) U.S. Cl.
CPC ...... *A61C 17/0205* (2013.01); *A61C 17/0202* (2013.01); *B67D 7/0294* (2013.01)

(58) Field of Classification Search
CPC ............ A61C 17/0205; A61C 17/0202; B67D 7/0288; B67D 7/0294
See application file for complete search history.

(56) References Cited

U.S. PATENT DOCUMENTS 5,346,324 A * 9/1994 Kuo .................. A46B 11/0055
                                                      401/146
6,622,333 B1 * 9/2003 Rehkemper ............ A61C 17/30
                                                      15/22.1
6,644,878 B2 * 11/2003 Hall ....................... A61C 17/36
                                                      401/146

(Continued)

FOREIGN PATENT DOCUMENTS

JP    H04306452 A     10/1992
KR    101410048 B1    6/2014

*Primary Examiner* — Nicolas A Arnett

(57) ABSTRACT

An automatic filling mechanism for use in conjunction with a hand-held fluid droplet appliance (10) for dental cleaning, the automatic filling mechanism having a door (42) to a chamber (40) in the hand held fluid droplet appliance (10) for holding fluid, the door having a female liquid inlet port (44) and a female liquid and air exit interface (46) having a snorkel system (80) attached thereto that is inserted into the chamber (40) that is used to fill the chamber (40) with fluid (112) from a reservoir (110) on a docking and charging station (100) when the hand held fluid droplet appliance (10) is inserted into a cradle (160) on the docking and charging station (100).

13 Claims, 8 Drawing Sheets

(56) References Cited

U.S. PATENT DOCUMENTS

| | | | | |
|---|---|---|---|---|
| 6,689,078 B1* | 2/2004 | Rehkemper | ............ | A61C 17/30 15/29 |
| 7,080,980 B2* | 7/2006 | Klupt | ................... | A61C 17/222 15/167.1 |
| 7,264,026 B2* | 9/2007 | Gruber | ................. | A46B 11/063 141/113 |
| 8,317,424 B2* | 11/2012 | Chenvainu | ............ | A61C 1/0061 401/188 R |
| 8,813,291 B2* | 8/2014 | Gatzemeyer | ....... | A61C 17/0202 15/24 |
| 9,980,793 B2* | 5/2018 | Wagner | .............. | A61C 17/0202 |
| 2005/0004498 A1* | 1/2005 | Klupt | ................... | A61C 17/222 601/162 |
| 2005/0271531 A1* | 12/2005 | Brown, Jr. | ............ | A61C 1/0061 417/474 |
| 2005/0272001 A1 | 12/2005 | Blain et al. | | |
| 2005/0272002 A1* | 12/2005 | Chenvainu | ............ | A61C 1/0061 433/80 |
| 2006/0078844 A1* | 4/2006 | Goldman | ............. | A61C 1/0084 433/80 |
| 2012/0021375 A1 | 1/2012 | Binner et al. | | |
| 2014/0038127 A1* | 2/2014 | Gatzemeyer | ....... | A61C 17/0202 433/82 |
| 2017/0373517 A1* | 12/2017 | Johanski | ................. | H02J 7/025 |
| 2018/0000572 A1* | 1/2018 | Johanski | ............ | A61C 17/0202 |

\* cited by examiner

AUTOMATIC FILLING MECHANISM AND METHOD FOR A HAND-HELD ORAL CLEANING DEVICE

CROSS-REFERENCE TO PRIOR APPLICATIONS

This application is the U.S. National Phase application under 35 U.S.C. § 371 of International Application No. PCT/IB2015/059756, filed on Dec. 18, 2015, which claims the benefit of U.S. Provisional Patent Application No. 62/097,261, filed on Dec. 29, 2014. These applications are hereby incorporated by reference herein.

BACKGROUND

This invention relates generally to hand-held oral cleaning devices using a fluid droplet spray for cleaning of the interproximal areas of the teeth with such a spray. With oral healthcare, one generally thinks of simply brushing one's teeth. However, brushing of one's teeth, alone, does not clean interproximal areas of the teeth very well. Accordingly, dentists recommend flossing or other mechanisms in addition to brushing for improved cleaning of the interproximal spaces. Several oral cleaning devices are on the market that can be used at home. Oral cleaning devices using a spray of liquid droplets to clean dental regions of the teeth, including interproximal areas, are known. In many such appliances, a stream of high velocity gas is used to create the liquid droplets when liquid is brought into contact with the air stream, such as by a pump or other arrangement. One such device for home use is the Philips Sonicare AirFloss™ flosser (manufactured by Koninklijke Philips Electronics, N.V.). While the system is effective, one comment by users is that the chamber of liquid in the hand-held device needs intermittent refilling with water, mouthwash or other fluid, typically after just a few cleanings.

Accordingly, it would be desirable to have a mechanism for refilling the hand-held oral cleaning device with additional fluid easily between uses, while also enabling charging of the hand-held oral cleaning device.

SUMMARY OF THE INVENTION

Accordingly there is disclosed herein an automatic filling mechanism for a hand-held fluid droplet appliance for dental cleaning for use in conjunction with a docking and charging station having a reservoir for holding a larger amount of fluid than can be held in the chamber of the hand-held appliance, the mechanism being used for automatically refilling the fluid chamber on the hand-held fluid droplet appliance from the larger reservoir on the docking and charging station when the hand-held appliance is mounted into the docking and charging station.

Generally, in one aspect, an automatic filling mechanism for filling a fluid chamber in a hand-held fluid droplet appliance designed to be coupled to a docking and charging station have a fluid reservoir is provided. The automatic filling mechanism includes a door for the chamber that can be opened, the door having an O-ring around the outer perimeter thereof to prevent leaking of fluid, the door having a first female port there through which is an inlet port for receiving liquid from the docking and charging station fluid reservoir into the chamber of the hand held appliance, and a second female port there through that is a liquid and air exit interface having a snorkel tube of a snorkel system attached to the second port, the snorkel system, the snorkel tube having another end that is open and is positioned to be in the top portion of the chamber in the hand held appliance, the snorkel system used for exiting air and excess fluid from the chamber as fluid enters the chamber through the first female port from the fluid reservoir in the docking and charging station.

According to an embodiment, flexible sealing portions surround the first and second ports of the automatic filling mechanism to prevent leakage of fluid.

According to an embodiment, at least one check valve is connected to at least one of the first or second ports to control the automatic filling process and provide a shut-off.

According to an embodiment, a hard plastic tip is provided at the open end of the snorkel tube to help ensure proper positioning of the snorkel system within the chamber of the hand held appliance.

According to an embodiment, the hard plastic tip at the open end of the snorkel tube has a mechanism to reduce buildup of crystals from the fluid for helping to ensure the snorkel tube does not clog, such as a v-cut shape along the top edge, or one or more holes cut through the plastic tip.

According to an embodiment, the chamber has an asymmetrical shape so that the snorkel system can only be inserted in the proper orientation.

According to an embodiment, the snorkel system has an internal spring in at least a portion of the snorkel tube to keep the snorkel system properly oriented in the chamber.

According to an embodiment, the snorkel system has an air permeable membrane at the open end of the snorkel tube.

According to another aspect, a method of automatically filling a fluid chamber of hand-held fluid droplet appliance from a fluid reservoir on a docking and charging station is provided. The hand held fluid droplet appliance is configured to be filled when docked in the docking and charging station. The hand held appliance is inserted in a cradle mechanism on the docking and charging station that aligns male ports on the docking and charging station fluid reservoir with female ports on the cover of the fluid chamber of the hand-held fluid droplet appliance. When the ports are properly aligned and coupled, fluid from the fluid reservoir on the docking and charging station flows into the chamber of the hand held appliance through one set of coupled ports, and air in the chamber is evacuated through the other set of conjoined ports.

According to another aspect, one or more safety mechanisms are provided to prevent overfilling of the liquid chamber.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

DETAILED DESCRIPTION OF THE INVENTION

Figure 1A:
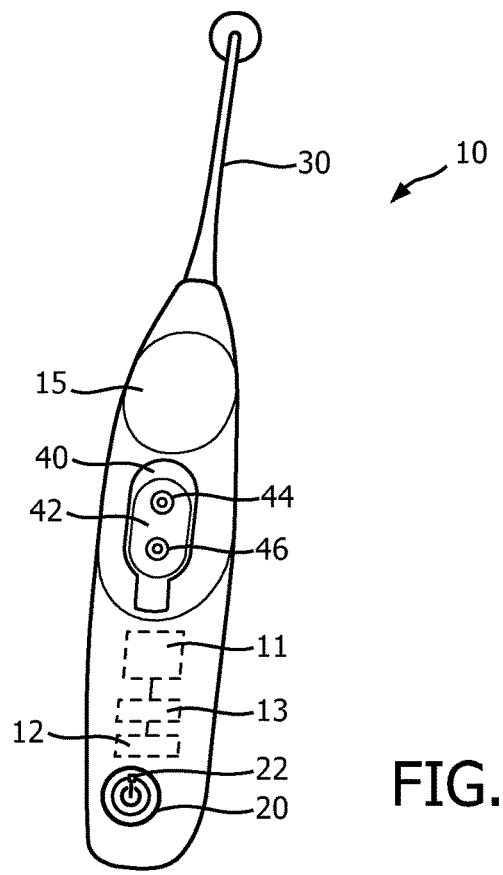
FIG. 1A is a view of a hand-held appliance as described herein.

The present invention pertains to a hand-held fluid droplet appliance 10, as described and shown herein, which produces a spray of liquid droplets which is used to clean the interproximal spaces between teeth. FIG. 1A shows a hand-held fluid droplet appliance 10 which uses a mechanical system to create a liquid droplet spray for oral cleaning. The appliance includes a motor and gear train arrangement 11 powered by a battery 12. A control unit 13 is included between the battery 12 and the motor 11 for control of the operation of the hand-held fluid droplet appliance 10. In operation, the hand-held fluid droplet appliance 10 is turned on or off with a power button 20. The power button 20 typically includes an illuminated portion 22 that is used to indicate that the hand-held fluid droplet appliance 10 is on, or is being charged. The hand-held fluid droplet appliance 10 includes an elongated nozzle 30 which extends outwardly from the appliance, through which a spray of liquid droplets is directed through an orifice for cleaning action against dental regions of the teeth and other areas of the oral cavity. A chamber 40 for water or other liquid is also present in the hand-held appliance. Liquid in the chamber 40 is mixed with air and propelled out through an orifice within the nozzle 30 by means of the motor and gear train arrangement 11. An actuator button 15 or similar element is used to actuate the appliance and generate sprays of air and liquid. The chamber 40 can be refilled manually by opening the door 42 to the chamber and pouring in liquid from a container or direct from a fluid source (i.e. a water faucet). Additionally, with the present invention, the hand-held fluid droplet appliance 10 can also be filled automatically when connected to a docking and charging station 100 (shown in FIG. 2) that has a liquid reservoir 110. Various aspects of the hand-held fluid droplet appliance 10 are disclosed and claimed in other patents and patent applications of the assignee.

Figure 1B:
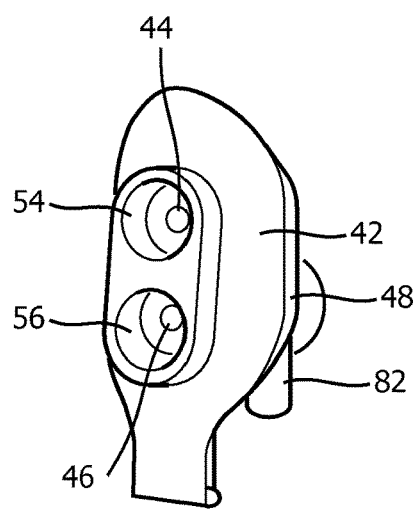
FIG. 1B is a detailed view of the chamber cover of the hand-held appliance of the present invention.

FIG. 1B provides a more detailed view of the door 42 of the chamber 40 in the hand-held fluid droplet appliance 10. The door 42 of the present invention includes two female ports 44, 46, each of which is surrounded by a flexible sealing portion 54, 56, to provide a waterproof seal and prevent leaking. The dual-port arrangement allows for a recirculating fill flow. The first female port 44 is typically a liquid inlet interface which allows liquid to flow into the chamber 40 from the reservoir 110 on the docking and charging station 100, and the second female port 46 is typically the liquid and air exit interface, although other arrangements are also possible. The liquid transfer system is described in greater detail below. Because the ports are used for the transfer of liquid, the door 42 on the chamber 40 is further sealed with an O-ring 48 for additional protection against leakage.

Figure 2A:
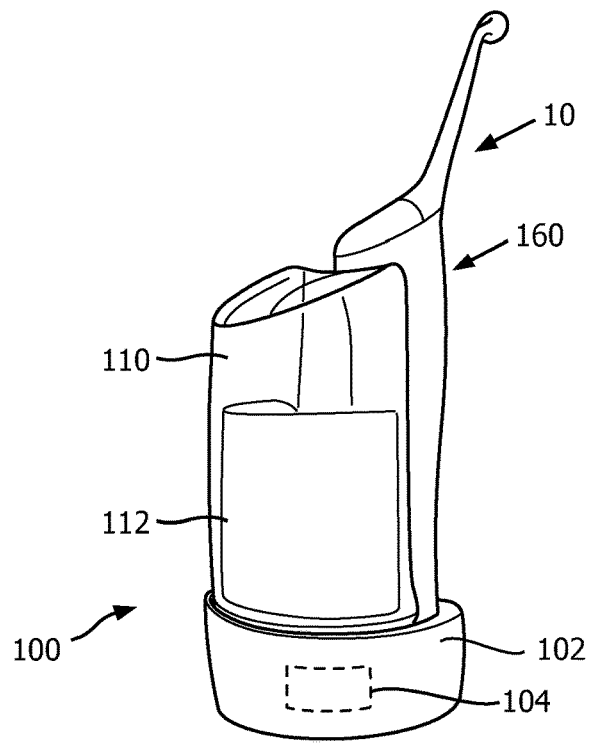
FIG. 2A is a side view of the docking and charging station of the present invention with the hand-held appliance mounted thereon for refilling and charging.
Figure 2B:
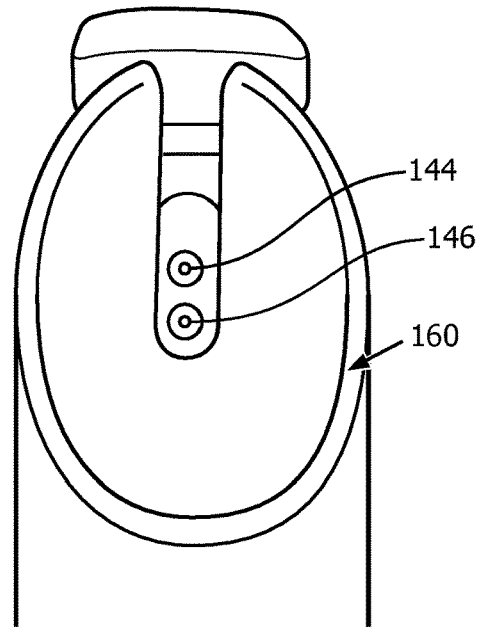
FIG. 2B is a top view of the docking and charging station of the present invention showing the cradle and male ports of the docking and charging station.
Figure 2C:
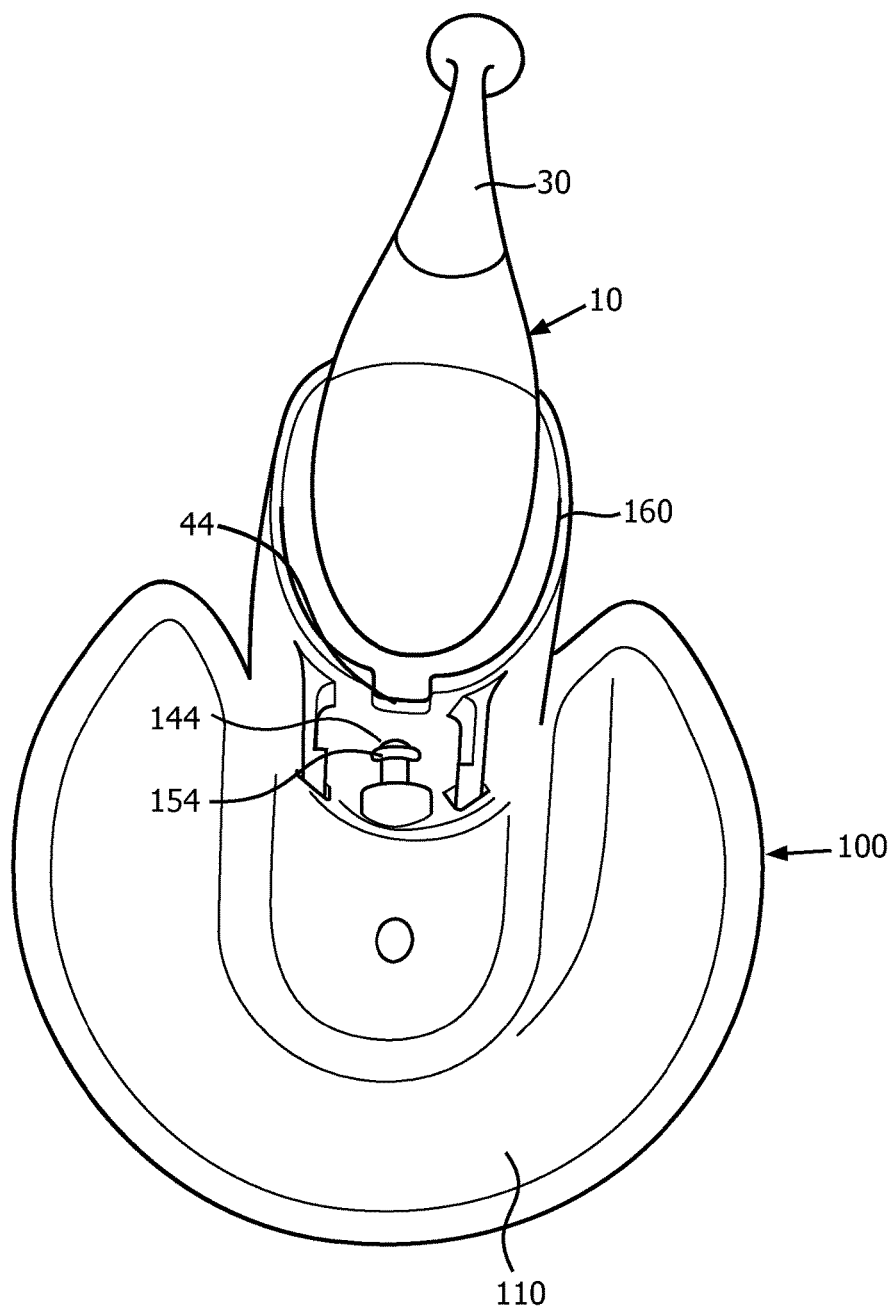
FIG. 2C is a top view of the docking and charging station of the present invention with the hand held appliance inserted into the cradle, but with the hand-held appliance not yet joined to the fluid reservoir by means of the male ports of the docking and charging station.
Figure 3A:
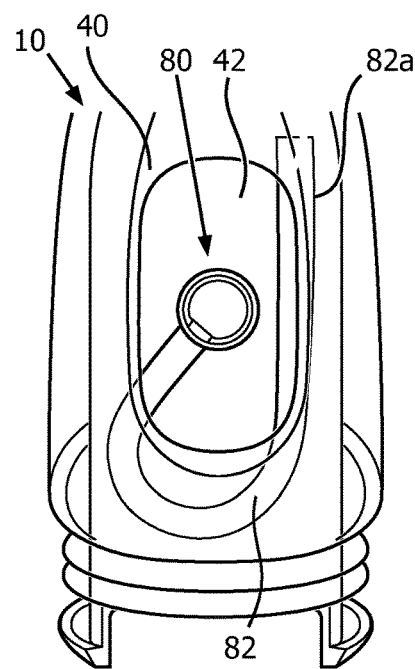
FIGS. 3A and 3B are front and side cut-away views of the snorkel system of the present invention and the connection of the hand-held appliance to the fluid reservoir of the docking and charging station.
Figure 3B:
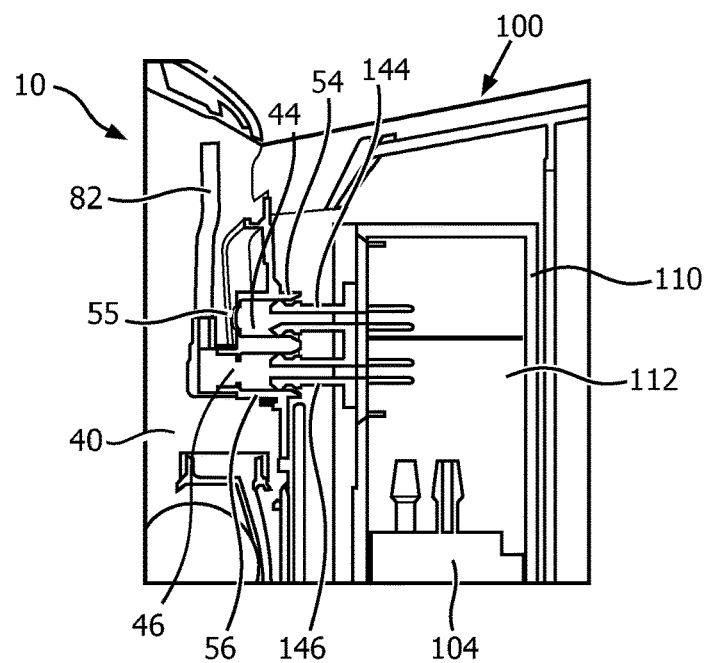

As disclosed herein, the present invention is intended to enable use of the hand-held fluid droplet appliance 10 with a docking and charging station 100 for automated refilling and charging of the hand-held fluid droplet appliance 10. The docking and charging station 100 is shown in FIGS. 2A through 2C. As can be seen in FIG. 2A, the docking and charging station 100 includes a larger reservoir 110 for holding water, mouthwash, antimicrobial fluids, or other fluids 112, and a pump 104 for pumping liquid out of the docking and charging station reservoir in the base 102 of the docking and charging station 100. When the hand-held fluid droplet appliance 10 is mounted into the cradle 160 of docking and charging station 100, fluid 112 from the docking and charging station reservoir 110 can be used to fill the chamber 40 on the hand-held fluid droplet appliance 10. As shown in FIG. 2B, the docking and charging station 100 has two male ports 144 and 146, which engage two respective female ports 44, 46 in the hand-held appliance, which can be seen in FIGS. 1A and 1B. As can be seen in FIGS. 2C and 3B, when the hand held fluid droplet appliance 10 is inserted in the cradle 160 of the docking and charging station 100, the female ports 44, 46, of the hand held fluid droplet appliance 10 align with the male ports 144, 146 of the docking and charging station 100 and will be mated when the cradle 160 is in the proper position. The female ports 44, 46 and the male ports 144, 146 are typically surrounded by a flexible sealing mechanism, O-ring or other device 54, 56 and 154, 156, respectively, that prevents leaking of fluid through the ports. The dual-port arrangement allows for a recirculating fill flow. When the hand-held fluid droplet appliance 10 is connected to the docking and charging station 100, it can also be electrically recharged.

When the hand-held fluid droplet appliance 10 is docked into the docking and charging station 100, the hand-held appliance is intended to automatically fill the chamber 40 from the reservoir 110 on the docking and charging station 100, assuming there is fluid 112 in the docking and charging station reservoir 110. The main elements of the present invention are the door 42 to the chamber 40 of the hand held fluid droplet appliance 10 with two female ports 44, 46, as shown in FIG. 1B, and a "snorkel system" 80 for the hand held fluid droplet appliance 10 that is part of the door 42 to the chamber 40, as shown in FIG. 3A. The two female ports 44, 46 are designed to interface with the two male ports 144 and 146 on the docking and charging station 100 for refilling of the chamber 40 of the hand-held fluid droplet appliance 10.

As disclosed herein, in order for the chamber 40 on the hand-held fluid droplet appliance 10 to be refilled effectively from the larger reservoir 110 on the docking and charging station 100 when the hand-held fluid droplet appliance 10 is connected to the docking and charging station 100, there needs to be a way to vent the air in the chamber 40 in the hand-held appliance to allow for refilling from the reservoir 110 in the docking and charging station. As seen in FIGS. 1B and 3A, the snorkel tube 82 of the snorkel system 80 is connected to the lower female port 46 in the door 42 of hand-held fluid droplet appliance 10. The top end 82a of the snorkel tube rests at the top of the chamber 40, an area that is emptied of fluid as the hand held device is used and fluid is sprayed into the oral cavity. This allows for air at the top of the chamber 40 to be evacuated while liquid is being delivered into the chamber 40 from the reservoir 110. It can be appreciated that while the arrangement shown in the figures of this application indicate upper and lower female ports 44, 46, with the snorkel system 80 connected to the lower female port 46, other arrangements are also possible, such as the snorkel system 80 being connected to the upper female port 44, or female ports 44, 46 being arranged side by side, or in other configurations.

Figure 7:
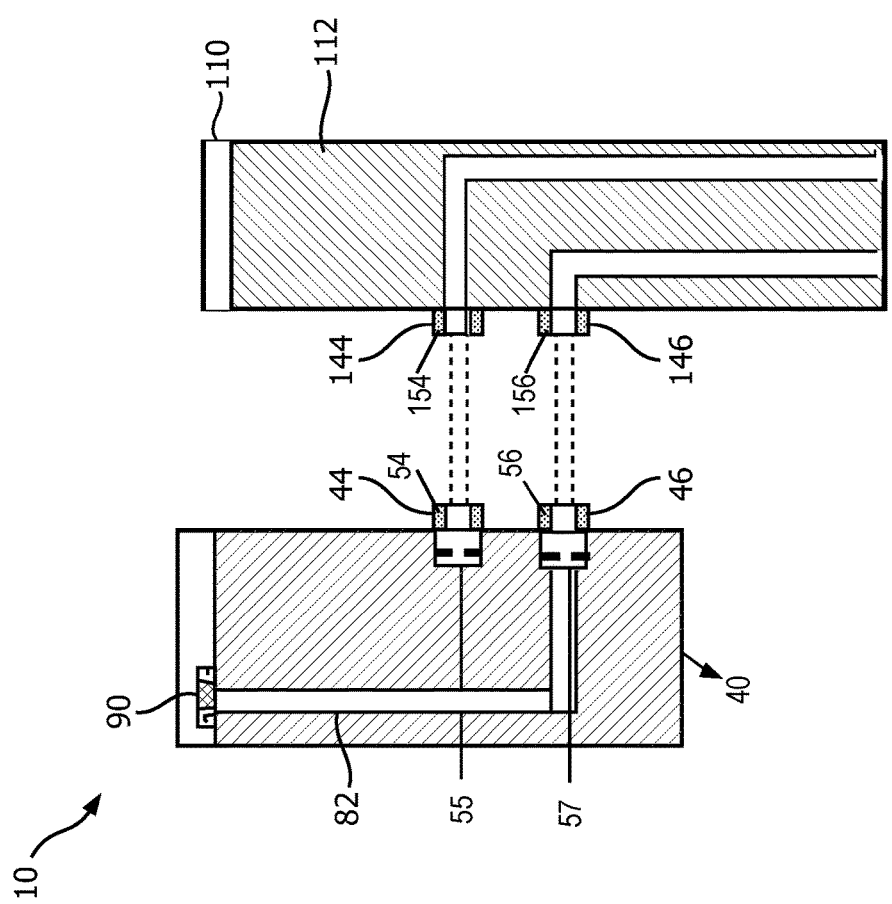
FIG. 7 is a representational view of another arrangement of a system of the present invention.

As shown in FIG. 3B, and as can also be seen in FIG. 7, the fill interface mechanism consists of the two male ports 144 and 146 on the docking and charging station, which engage the two respective female ports 44, 46 of the present invention in the hand-held fluid droplet appliance 10. The dual-port arrangement allows for a recirculating fill flow. One female port 44, is a liquid inlet interface with a check valve 55 which allows liquid to flow through the female port 44 when the check valve 55 is open, and it typically has an O-ring or flexible rubber seal 54 around the port to prevent leakage. The second female port 46 is the liquid and air exit interface that has a flexible sealing portion 56 to close the port and prevent leakage, and may also have a check valve, micro switch, or other safety mechanism 57 to close the port and prevent leakage or overflow and allow operation only when the hand held fluid droplet appliance 10 is properly docked to the docking and charging station 100. As disclosed herein, in order for the chamber 40 on the hand-held fluid droplet appliance 10 to be refilled effectively from the larger reservoir 110 on the docking and charging station 100 when the hand-held fluid droplet appliance 10 is connected to the docking and charging station 100, there needs to be a way to vent the chamber 40 in the hand-held fluid droplet appliance 10 to allow for filling of the chamber 40 from the reservoir 110 in the docking and charging station 100. When the hand-held fluid droplet appliance 10 is properly connected into the docking and charging station 100 as shown in FIG. 3B, fluid 112 is delivered into the chamber 40 from the reservoir 110 through the liquid inlet interface created when ports 144 and 44 are connected; check valve 55 only allows liquid to flow through the ports 44, 144 when the check valve 55 is open, serving as a safety mechanism. Similarly, safety mechanism 57, if present, which can also be a check valve, a micro switch or some other arrangement of device, only allows liquid to flow through the ports 46, 146, when the ports are properly aligned and connected to prevent leakage or overflow. The snorkel tube 82 is connected female port 46, the liquid and air exit interface in the door 42 of hand-held fluid droplet appliance 10. The top end 82a of the snorkel tube rests at the top of the chamber 40. This allows for air at the top of the chamber to be evacuated while new liquid is being delivered into the lower portion of the chamber 40. This arrangement allows displaced air and over-fill liquid to return to the reservoir 110 in the docking and charging station 100 during filling operations. Therefore, no device is needed for detecting the fluid level in the chamber 40 of the hand-held fluid droplet appliance 10.

Figure 4A:
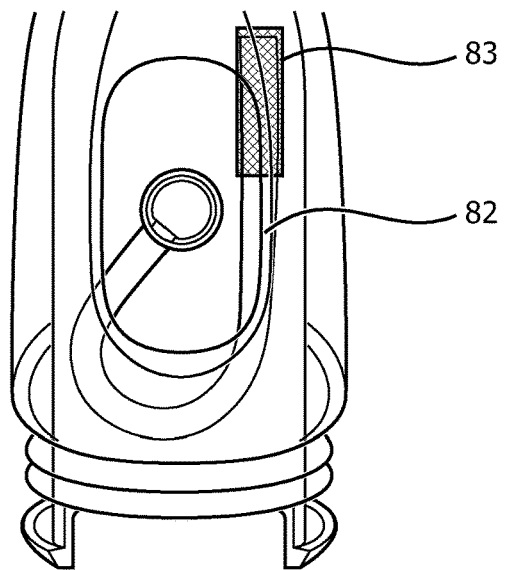
FIGS. 4A-4C are front cutaway and front views of a positioning option for the snorkel system of the present invention.
Figure 4B:
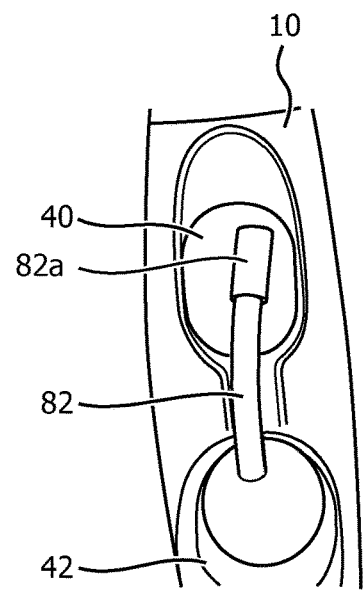
Figure 4C:
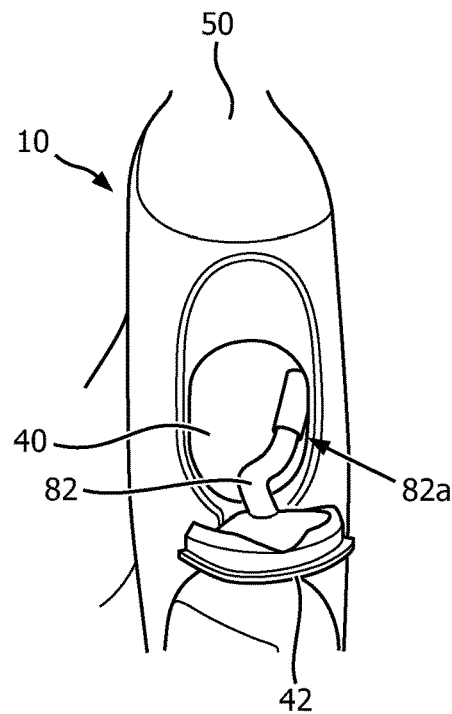

FIGS. 4A-4C show various arrangements the snorkel system 80 that help ensure that the snorkel system 80 is properly positioned in the chamber 40, and that the chamber door 42 is not inadvertently inserted upside down, thereby causing misplacement or misalignment of the snorkel tube 82. As shown in FIG. 4A, by providing a hard tip 83 of correct dimensions with respect to the opening and chamber size at the top end 82a of the snorkel tube 82, this will help ensure the open tip of the snorkel is always at the top of the chamber and is not accidentally inserted incorrectly. The hard tip 83 must be of the correct size that it remains upright and does not fold down the snorkel tube 82 due to the weight of the hard tip, is also large enough to remain at the top of the chamber 40, and does not pull out easily when the chamber door 42 is opened, such as for manual refilling. The proper sized hard tip 83, combined with curvature, orientation, and stiffness of the snorkel tube 82 helps to force the top end 82a of the snorkel tube 82 into an upright position at the top of the chamber 40. In another arrangement of the present invention, as shown in FIG. 4B, the chamber 40 is asymmetrically sized internally such that a larger portion of it is above the top of the opening to help ensure the snorkel tube 82 cannot be placed in the chamber 40 upside down and the top end 82a of the snorkel tube 82 will always be at the top end of the chamber 40. Additionally, in an arrangement shown in FIG. 4C, the chamber 40 is asymmetrically sized internally such that a larger portion of it is to one side of the opening, such that the snorkel tube 82 will be naturally biased to fit in one side of the chamber 40, thus further ensuring proper orientation.

Figure 5:
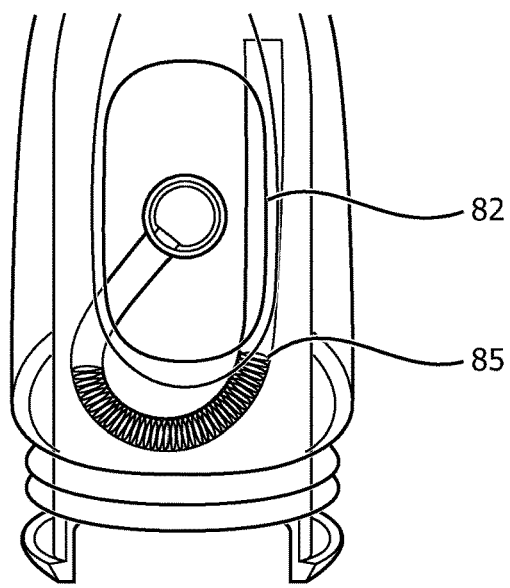
FIG. 5 is a front cutaway view of an anti-kink option for the snorkel system of the present invention.

Another option is an anti-kink feature for the present invention, as shown in FIG. 5, which can be provided to prevent the snorkel tube 82 from bending and becoming blocked or kinked inside the chamber 40, thereby preventing proper operation. By inserting an internal spring 85 in the portion of the snorkel tube 82 that should reside in the lower portion of the chamber, it will help to maintain the proper curvature of that portion of the snorkel tube 82, and prevent kinking of the snorkel tube 82. The internal spring 85 also has the added benefit of helping to maintain the snorkel tube in the proper position and orientation within the chamber 40.

Figure 6A:
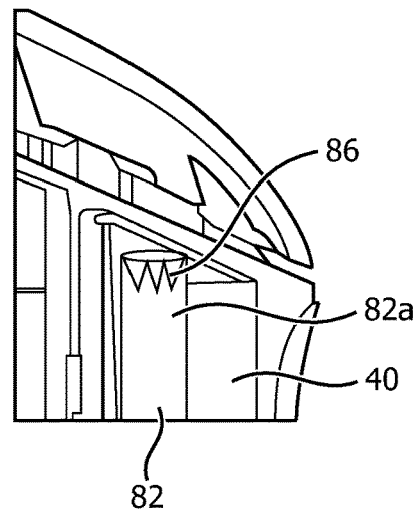
FIGS. 6A and 6B are side cutaway views of arrangements of anti-clog options for the snorkel system of the present invention.
Figure 6B:
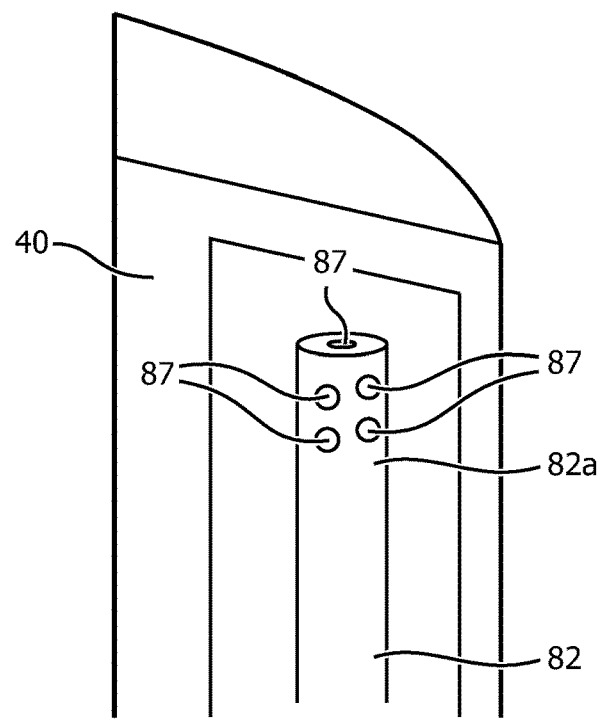

Additionally, a mechanism for ensuring the snorkel tube 82 and ports 44, 46, 144, 146 do not clog is desirable, especially when fluid 112 such as mouthwash or antimicrobial liquids, which may have more mineral content, are used in the docking and charging station reservoir 110, as these can dry and crystalize. It was determined that by modifying the top end 82a of the snorkel tube 82, such as the top having a v-cut edge 86 such as shown in FIG. 6A, or inserting one or more holes 87 in the top end 82a, as shown in FIG. 6B, the flow path of the liquid is broken up, thereby preventing formation of crystals or clogging the flow of liquid. This can help ensure continued efficient operation of the mechanism of the present invention.

Another arrangement of the present invention is depicted in FIG. 7. In which an air permeable membrane 90 is attached to the top end 82a of the snorkel tube 82. This will allow the air present in the chamber 40 to be evacuated through the snorkel tube 82 and through the ports 46, 146, but does not let any fluid pass through the membrane 90. Further, this arrangement may eliminate the requirement for a valve or safety device 57 on port 46, because no fluid passes through the port, although one is depicted in FIG. 7. This arrangement may also eliminate the need for other additional overflow or shutoff safety mechanisms in the docking and charging station 100.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. An automatic filling mechanism for a hand-held fluid droplet appliance for oral cleaning, the appliance designed to be coupled to a docking and charging station having a fluid reservoir, the automatic filling mechanism comprising:
   a chamber for holding fluid having a door into the chamber that can be opened,
   the door having an O-ring around an outer perimeter thereof,
   and first and second female ports located therethrough,
   wherein the first female port comprises an inlet for receiving fluid; and
   wherein the second female port comprises a liquid and air exit interface having a snorkel system attached thereto, the snorkel system comprising a snorkel tube attached to the second port at a first end thereof, a second end of the snorkel tube being open and resting at a top of the chamber, the second port and snorkel mechanism used for exiting air and excess fluid from the chamber as fluid enters the chamber through the first port from the fluid reservoir.

2. The automatic filling mechanism of claim 1, comprising flexible sealing portions surrounding first female port and second female port respectively.

3. The automatic filling mechanism of claim 1, comprising at least one check valve coupled to first female port or second female port respectively.

4. The automatic filling mechanism of claim 3 comprising a safety mechanism connected to second port.

5. The automatic filling mechanism of claim 1 further including a hard tip at the second end of the snorkel tube to help ensure proper positioning of the snorkel system within the chamber.

6. The automatic filling mechanism of claim 5 wherein the hard tip at the second end of the snorkel tube has a v-cut edge.

7. The automatic filling mechanism of claim 5 wherein the hard tip at the second end of the snorkel tube has at least one hole cut there through.

8. The automatic filling mechanism of claim 1 wherein the chamber is asymmetrical.

9. The automatic filling mechanism of claim 1 further including an internal spring in at least a portion of the snorkel tube.

10. The automatic filling mechanism of claim 1 further comprising an air permeable membrane at the second end of the snorkel tube.

11. A method of filling a hand-held fluid droplet appliance from a docking and charging station having a pump, a fluid reservoir, first and second male ports, and a cradle mechanism for receiving the hand-held fluid droplet appliance, the appliance being for oral cleaning, the method comprising the steps of:
   docking the hand-held fluid droplet appliance into the cradle mechanism on the docking and charging station;
   engaging two female ports on a door of a chamber of the hand-held fluid droplet appliance to two respective male ports on the docking and charging station;

pumping fluid from the reservoir on the docking and charging station through conjoined male and female inlet ports into the chamber of the hand-held fluid droplet appliance; and evacuating air and any excess fluid from the chamber of the hand-held fluid droplet appliance through the conjoined male and female liquid and air exit interface ports;

wherein a snorkel tube connected to female liquid and air exit interface port is inserted in the chamber to ensure complete evacuation of air from the chamber and enable complete filling with liquid therein.

12. The method of claim 11 wherein a valve is provided, the valve configured to only allow liquid to flow through the male and female inlet ports when the valve is open.

13. The method of claim 11 wherein the cradle mechanism is configured to ensure proper alignment of the male ports of the docking and charging station with the respective female ports of the hand held fluid droplet appliance prior to filling the hand-held fluid droplet appliance.

\* \* \* \* \*